(12) United States Patent
Haikel et al.

(10) Patent No.: US 8,770,970 B2
(45) Date of Patent: Jul. 8, 2014

(54) DEVICE FOR PLACING A DENTAL SPLINT

(75) Inventors: Youssef Haikel, Strasbourg (FR);
Abd-Al-Qadir Maadi, Mulhouse (FR);
Karim Maadi, Mulhouse (FR);
Mahfoud Maadi, Mulhouse (FR)

(73) Assignee: Dynadent Sarl, Mulhouse (FR)

( * ) Notice: Subject to any disclaimer, the term of this patent is extended or adjusted under 35 U.S.C. 154(b) by 0 days.

(21) Appl. No.: 13/509,146

(22) PCT Filed: Nov. 9, 2010

(86) PCT No.: PCT/FR2010/000745
§ 371 (c)(1),
(2), (4) Date: May 10, 2012

(87) PCT Pub. No.: WO2011/058243
PCT Pub. Date: May 19, 2011

(65) Prior Publication Data
US 2012/0225397 A1    Sep. 6, 2012

(30) Foreign Application Priority Data

Nov. 13, 2009 (FR) ...................................... 09 58019

(51) Int. Cl.
*A61C 7/00* (2006.01)
(52) U.S. Cl.
USPC .......................................................... 433/18
(58) Field of Classification Search
USPC ......... 433/3, 18, 19, 22, 24, 49, 53, 148, 149, 433/155; 606/54, 105; 602/17, 902
See application file for complete search history.

(56) References Cited

U.S. PATENT DOCUMENTS

| | | | | |
|---|---|---|---|---|
| 4,090,299 A * | 5/1978 | Williams | ......................... | 433/18 |
| 4,202,328 A * | 5/1980 | Sukkarie | ......................... | 433/18 |
| 4,318,694 A | 3/1982 | Klein | | |
| 6,257,884 B1 * | 7/2001 | Chang | ............................. | 433/18 |
| 6,960,082 B2 * | 11/2005 | Besek | ............................. | 433/39 |
| 2006/0078849 A1 * | 4/2006 | Parks | ............................ | 433/215 |

FOREIGN PATENT DOCUMENTS

CA    1 259 866 A1    9/1989

* cited by examiner

*Primary Examiner* — Cris L Rodriguez
*Assistant Examiner* — Matthew Seward
(74) *Attorney, Agent, or Firm* — Davis & Bujold PLLC; Michael J. Bujold

(57) ABSTRACT

A device (1) for placing a dental splint (2) which is intended to be fixed at the level of the lingual, palatal or vestibular surfaces of at least two adjacent teeth (10) to immobilize the teeth. The placing device (1) has at least one flexible and elongated guiding support (3) carrying the splint (2), at least one positioning element (4, 4'), mounted so as to slide on the guiding support (3) behind the splint (2), and arranged for being positioned substantially in front of an interproximal gap (9) between the at least two adjacent teeth (10). A pressing mechanism (5, 5') coupled to the positioning element (4, 4') and arranged to bring the positioning element (4, 4') close to the at least two adjacent teeth (10) to be interlocked, when pressed, to bring the splint (2) in contact and conform with the lingual, palatal or vestibular surfaces.

9 Claims, 5 Drawing Sheets

DEVICE FOR PLACING A DENTAL SPLINT

This application is a national stage completion of PCT/FR2010/000745 filed Nov. 9, 2010 which claims priority from French Application Serial No. 0958019 filed Nov. 13, 1012.

TECHNICAL SCOPE

The present invention relates to a device for placing a dental splint, said splint being in the form of a wire, a grid or a tape out of a flexible metallic, synthetic or fibrous composite material, said splint being intended to be fixed at the level of the lingual, palatal or vestibular surface of at least two adjacent teeth in order to immobilize them with respect to each other.

PRIOR TECHNIQUE

Dental splints are used to prevent and/or treat tooth mobility by maintaining the teeth in a determined position, close to the physiological position. They are used temporarily or permanently, in particular within the framework of periodontal or post-traumatic treatments, after an orthodontic treatment to stabilize the result, within the framework of the provisional replacement of one or two missing teeth, or also while waiting for an implant, during the healing period.

The principle of a dental splint is based on the interlocking of several teeth in order to immobilize them, while allowing the patient to practice interdental plaque control.

Different methods are used today to achieve this interlocking.

So, a splint in the form of a wire, a grid or a tape out of a flexible metallic, synthetic or fibrous composite material sealed by means of a composite material on the lingual or palatal surfaces of several adjacent teeth is commonly used. Another method consists in implanting, at the level of the concerned teeth, a ligature out of steel wire accommodated in a vestibular canal hidden with composite material. Furthermore, in order to remedy more specifically the mobility of the upper incisors and of the posterior teeth, another currently used method also consists in placing a thick orthodontic wire out of steel or polymer fibres in a pit or in a lingual or occlusal groove.

The practitioner has today different techniques at his disposal for placing such dental splints, called "direct" when he manufactures and adapts the splint directly on the patient, or "indirect" when a dental technician is to take in charge the manufacture of the splint, after making an impression of the concerned surface. The "indirect" techniques are used e.g. when the splint is to be placed in a groove.

Today, both the "direct" and "indirect" techniques do not give entire satisfaction.

So, the "direct" techniques imply that the practitioner adheres scrupulously to a complex and long operating protocol. During the first step of this protocol, he is to adjust the splint to the shape of the implantation surface, which he has to do by trial-and-error work until obtaining the appropriate shape. Such a way of proceeding is not only laborious for the specialist, it is also tiring for the patient. Once the splint is ready, the practitioner has to carry out a chemical treatment of the concerned surfaces of the teeth before sealing the splint on them embedding it in a composite material. Greatest care must be taken when carrying out these two last steps, in particular in order to achieve the best tooth/composite/splint interface possible, failing which the implantation will fail. Finally, even though they allow implanting a splint in one single session, the "direct" techniques show to be fastidious, constraining and delicate to implement, and they require a great dexterity of the practitioner.

The "indirect" techniques have the main disadvantage of requiring several work sessions separated by time intervals that may be more or less long, which is very constraining both for the patient and for the practitioner. So, at least one session must be planned, during which the practitioner prepares the teeth, to make for example a groove in them, before making an impression that he gives to a dental technician for the manufacture of a splint with the suitable shape. Another session must then be planned for the insertion of the splint in the grove. Another disadvantage of this kind of techniques lies in its high cost and its invasive character.

DESCRIPTION OF THE INVENTION

This invention aims to overcome the disadvantages mentioned above by proposing, for the placing of dental splints, a device allowing to carry out this operation very easily, quickly, accurately, without risk of error and in one single session. The invention aims in particular to propose a solution allowing, in only one single session, to adapt a dental splint to the morphology of the teeth and to hold it in close contact with these same teeth during the sealing phase To that purpose, the invention relates to a device of the kind mentioned in the preamble, characterized in that said placing device comprises at least one flexible and elongated guiding support carrying said splint, at least one positioning element, mounted so as to slide on said guiding support behind said splint, and intended for being positioned substantially in front of an interproximal gap between two consecutive teeth, and pressing means coupled to said positioning element and arranged to bring said positioning element close to the teeth to be interlocked when pressing, in order to bring said splint in contact with said lingual, palatal or vestibular surfaces to fit their shape.

According to a preferred embodiment, said pressing means include, for each positioning element, a wire arranged to pass in the interproximal gap between two consecutive teeth, while this wire forms an open loop and passes through said positioning element, said pressing means also including a locking element crossed by the two free ends of said wire and arranged to be located on the side of the teeth opposite to said splint, resting against an interproximal gap.

According to an embodiment variant, each positioning element comprises at least two passages that cross it from the rear to the front, respectively at the level of its upper side and of its lower side, to allow the passage of said wire loop.

According to another variant, each positioning element comprises at least one passage crossing it from top to bottom at the level of its rear side, to allow the passage of said wire loop.

In a particularly advantageous way, each positioning element has, at least at the level of its front side, which is intended to rest against an interproximal gap, a triangular cross-section.

Another feature of this invention is also defined by the fact that the wire is made out of a material chosen among the group comprising nylon, Teflon®, polyethylene, a combination of these materials.

Furthermore, according to an embodiment variant, the wire presents a surface treatment intended to improve its sliding coefficient.

According to a preferred embodiment, this invention is also characterized in that said locking element comprises at least two assembled parts that are mobile with respect to each other between an unpressed position and a pressed position, and arranged to lock said free ends of said wire in their pressed position.

In this case, an embodiment variant consists in that said parts making up the locking element are assembled by screwing.

Said parts comprise preferably a first threaded part comprising at least one inlet opening for said free ends of said wire, at least one internal channel for the passage of said ends, and at least one outlet opening for said ends, and a second tapped part arranged to cooperate with said threaded part and to lock said ends in the pressed position.

According to another variant, said parts of the locking element are snapped together.

In this case, said parts comprise a first part equipped with at least one hook and with at least one opening for the passage of the free ends of the wire, and a second part equipped with at least one opening for the passage of the free ends of the wire and with a seat arranged to receive said hook and lock said ends in the pressed position.

Advantageously, at least one of said parts presents, at least partly, a triangular cross-section at the level of its area intended for resting against an interproximal gap.

According to another embodiment, said locking element comprises a sleeve mounted tightly on said free ends of said wire.

Said sleeve is preferably made out of a material with a high friction coefficient, for example based on synthetic or natural rubber.

According to an additional feature of the device according to the invention, the guiding support comprises at each of its ends a socket for fastening the splint, at least one of these sockets being arranged to allow a longitudinal movement of said splint with respect to said guiding support.

Furthermore, according to another embodiment variant of the invention, said positioning element comprises two enlarged end sections connected together by means of a narrow central section comprising a slot for the passage of said splint, said positioning element being arranged to adopt a retracted rest position in which said end sections are close to each other and a stretched active position in which said end sections are distant from each other so that the central section passes in an interproximal gap in order to bring said splint in contact with the lingual, palatal or vestibular surface of said teeth.

According to an advantageous feature, said positioning element is made of one single part out of an elastic material, while at least said central section forms said pressing means.

An additional feature is defined by the fact that said end sections have, at least at the level of their front side, which is intended to rest against an interproximal gap, a triangular cross-section.

On the other hand, each of said end sections comprises at least one gripping means arranged to allow moving said end sections away from each other. In this case, said gripping means can include at least one cavity arranged to receive an end of a tool such as pliers.

In compliance with another feature of the invention, at least one of said end sections comprises a slot for the passage of said support.

According to a particularly advantageous embodiment variant, the guiding support is arranged to define a dental splint.

In this case, said guiding support is made out of a flexible metallic, synthetic or composite material.

In the preferred embodiment, this device for placing a splint is designed to be a single-use device.

BRIEF DESCRIPTION OF THE DRAWINGS

The present invention and its advantages will be better revealed in the following description of several embodiments given as non limiting examples, in reference to the drawings in appendix, in which.

Figure 1:
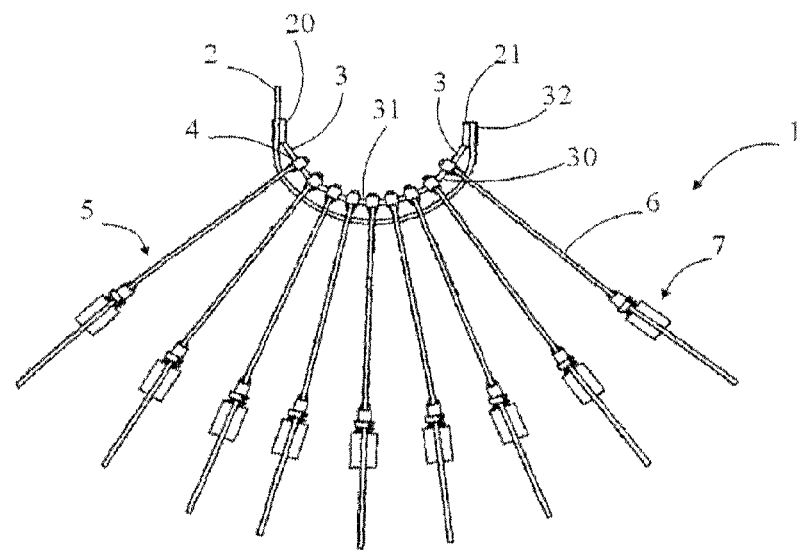
FIG. 1 represents a schematic top view of a first embodiment variant of a device for placing a dental splint according to the invention, equipped with positioning elements and pressing means in compliance with a first embodiment.
Figure 2:
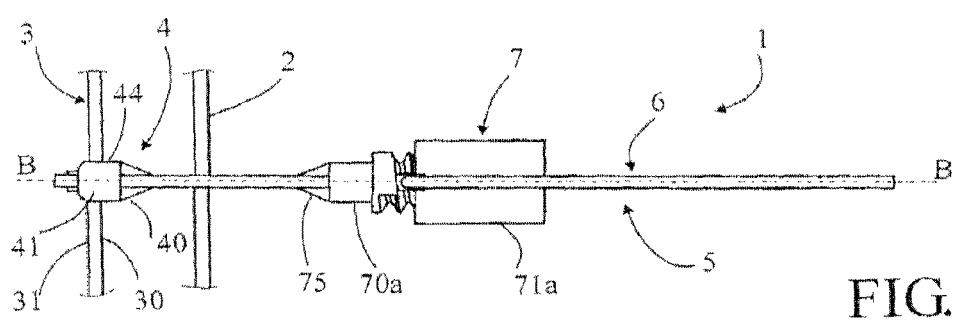
FIG. 2 is a partial top view of the device of FIG. 1.

Illustrations of the invention and different ways of realizing it:

Referring to the figures, the device 1 for placing a dental splint 2 comprises a guiding support 3 with an elongated shape, intended for being positioned, in the considered example (see FIG. 4-6), in front of the internal (lingual or palatal) surfaces of the teeth to be immobilized. This guiding support 3 is made out of a flexible synthetic material, in particular polyurethane or similar, has a front side 30 and a rear side 31, and comprises, at its ends 32, sockets 20, 21 for assembling it with splint 2, so that at least one of them, bearing reference 20, allows the latter a longitudinal movement with respect to said support 3.

Figure 4:
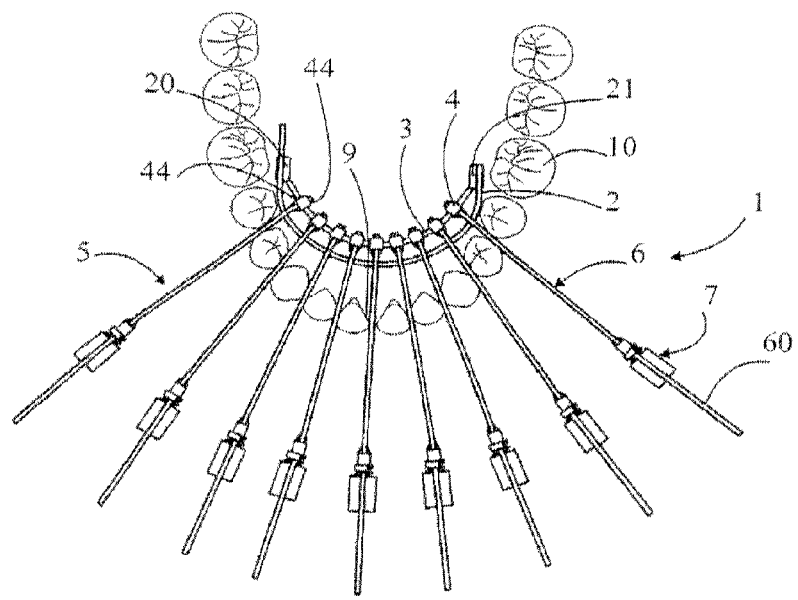
Figure 6:
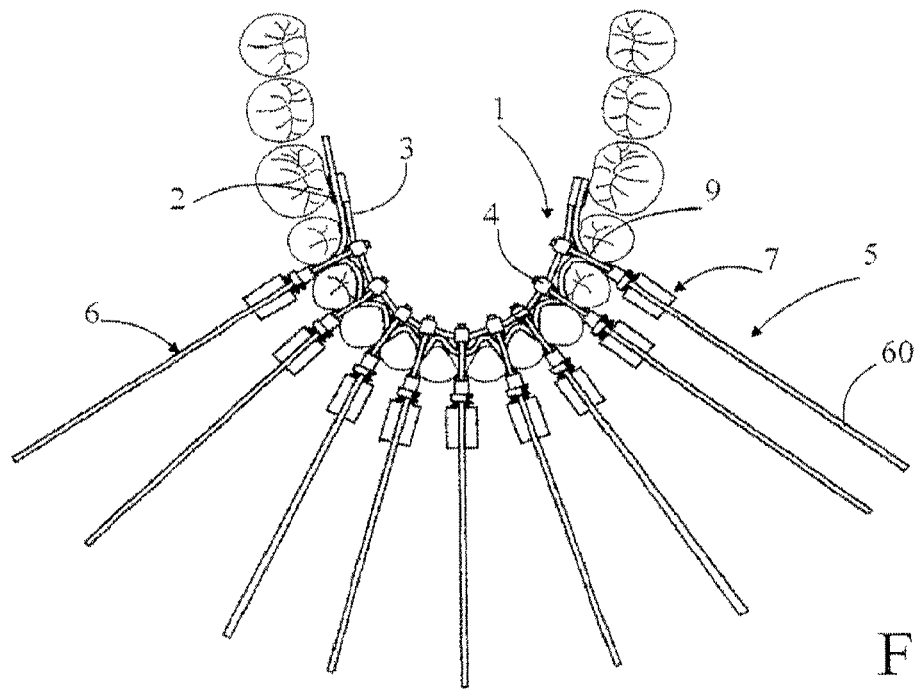

Several positioning elements 4, coupled each with a pressing element 5, are mounted so as to be able to slide on this guiding support 3 and are intended, as visible on FIGS. 4 and 6, to be positioned, when placing splint 2, in front of an interproximal gap 9 located between two consecutive teeth 10. In the represented example, these positioning elements 4 present a front side 40 with a substantially triangular cross-section, which is advantageously complementary of the natural conformation of said interproximal gap 9, which allows advantageously fitting perfectly the profile between the teeth, minimizing any possible pain and avoiding any injury when using device 1.

The positioning elements 4 are preferably made out of synthetic materials such as polyurethane, rubber or similar, compatible with medical use and presenting no risks of injuring the mouth.

In the embodiment variant represented on the various figures, each pressing element 5 comprises a wire 6 arranged to pass through interproximal gap 9, forming an open loop and passing through a positioning element 4. The pressing element 5 also comprises a locking element 7 mounted on the side of the free ends 60 of wire 6, intended to be positioned on the side of the teeth opposite to that where splint 2 is to be placed.

Figure 3:
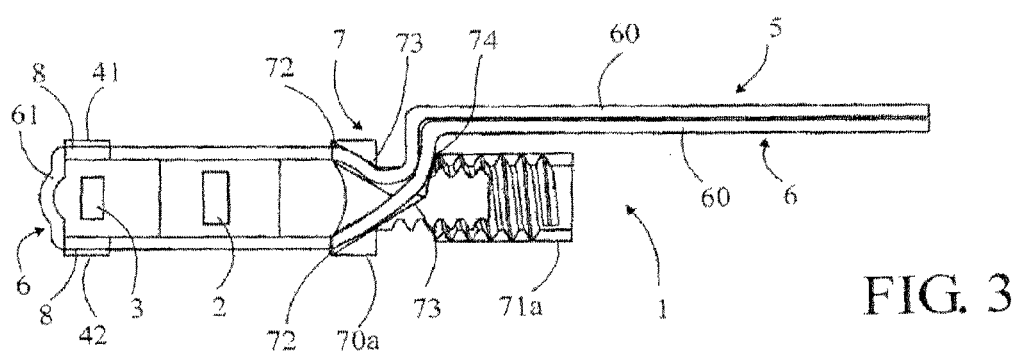
FIG. 3 is a cross-sectional view according to section BB of the partial view represented in FIG. 2, FIGS. 4 to 6 are top views of the device of FIG. 1 during its use, at three different stages of the process of placing a dental splint on the internal (lingual or palatal) surfaces of the teeth of a jaw.

The wire 6 passes through positioning element 4 at the level of passages 8, formed, in the represented example (see FIGS. 3 and 7), at the level of the upper side 41 and of the lower side 42 of positioning element 4, these passages 8 extending from the rear side 43 towards the front side 40 of the latter.

This way, a loop 61 of wire 6 passes behind the positioning element 4 of the guiding support 3 and on both sides of splint 2.

Other embodiment variants, allowing to achieve an equivalent configuration of wire 6, consist in providing at least one passage 8 crossing each positioning element 4 from top to bottom at the level of its rear side 43, or at least two passages 8 crossing it and ending at the level of its rear side 43, with the goal of locating the loop of the wire at the rear of the support.

Other variants may also be contemplated, in which each pressing element 5 comprises two wires 6 extending, according to a first example, one from the upper side 43, the other one from the lower side 42 of positioning element 4 and fastened on the latter by any suitable fastening means, in particular gluing, thermowelding or similar. According to another example, the two wires 6 can also pass through positioning element 4 at the level of four passages 8 arranged, for two of them, at the level of upper side 41 and for the two other ones at the level of lower side 42, these passages creating a communication between rear side 43 and front side 40, and being arranged substantially along the lateral sides 44 of positioning element 4.

Advantageously, and in order to prevent any risk of injury of the gum when placing splint 2, in particular at the level of the interproximal gap 9, the wire 6 is preferably made of dental floss that can be manufactured in a material chosen among the group comprising nylon, Teflon®, polyethylene, a combination of these materials or any similar material.

In order to facilitate its handling and improve further the comfort of the patient, the wire 6 may also include a surface treatment intended to improve its sliding coefficient, such as for example the application of a layer of a wax suitable for use in a mouth.

As it is clearly visible on FIGS. 2, 3, and 7 to 10, the locking element 7 comprises two assembled parts 70a and 71a or 70b and 71b that can be moved along the ends 60 of wire 6 to be located closer to or moved away from positioning element 4, so as to create a traction on wire 6 or to release it, moving the guiding support 3 respectively closer to or away from the lingual or palatal surfaces of the teeth 10. These parts 70a, 71a, 70b, 71b also allow achieving the locking of the ends 60 of wire 6, which is particularly advantageous in the pressed position that is required.

In the example represented on FIGS. 1 to 6, part 70a is a threaded part, assembled by screwing with a part 71a, which shows an internal thread suited to that purpose. The threaded part 70a has two inlet openings 72 for each of the free ends 60 of wire 6, two internal channels 73 for the passage of these ends 60 and an outlet opening 74 for these same ends. The locking element 7 is moved by hand along the free ends 60 of wire 6, holding the two free ends 60 of wire 6 in one hand and sliding with the other hand the locking element 7 in order to bring it closer to positioning element 4. It can finally be positioned so as to rest against the interproximal gap 9 in front of which this same positioning element 4 had been previously located, against the surfaces of the teeth opposite to the surfaces where splint 2 is to be implanted. To immobilize the locking element 7 in this tightened position, tapped part 71a is screwed on threaded part 70a to bring these two parts closer and thus lock the free ends 60 of wire 6 in position.

In the embodiment variant represented on FIGS. 7 to 10, part 70b is snapped in part 71b. Part 70b comprises two openings 77 for the passage of the free ends 60 of wire 6 and is equipped with a hook 76. Part 71b comprises four openings 79 (see FIG. 7) for the passage of the free ends 60 of wire 6 and a seat 78 receiving hook 76.

Figure 7:
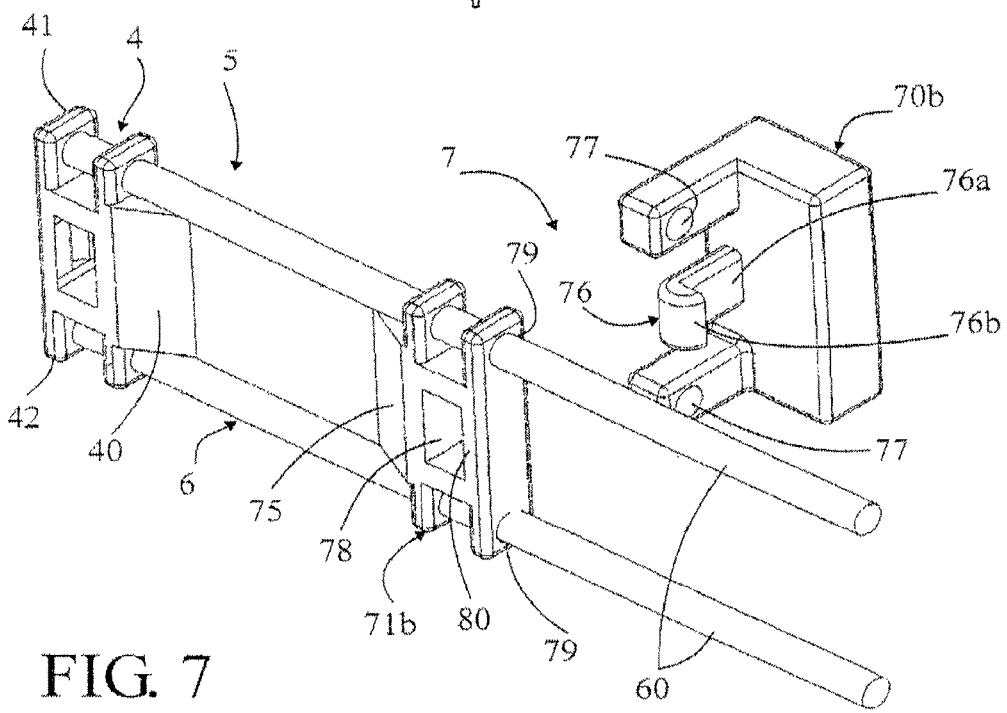
FIG. 7 is a perspective view of another embodiment of a positioning element and of the pressing means, in a dissociated state, FIG. 8 correspond to a front view of the positioning element and of the pressing means represented in FIG. 7, in an assembled state, FIGS. 9 and 10 correspond to top views of the view represented in FIG. 8, with the pressing means respectively in unlocked and locked position.
Figure 8:
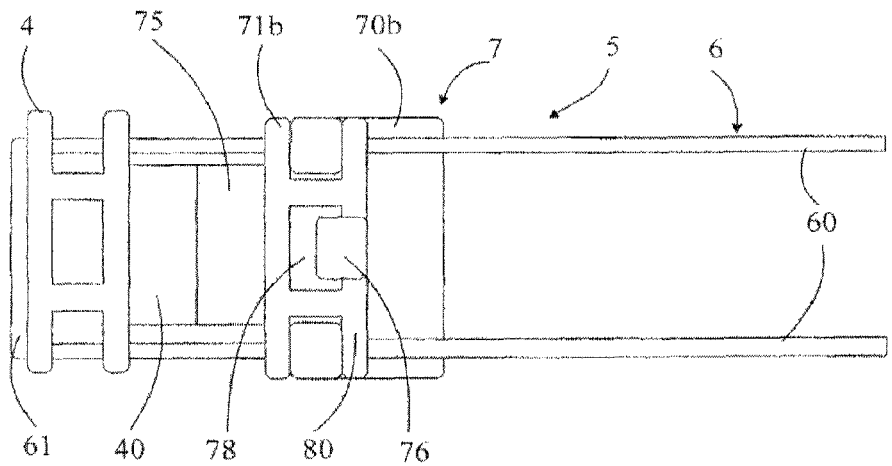
Figure 9:
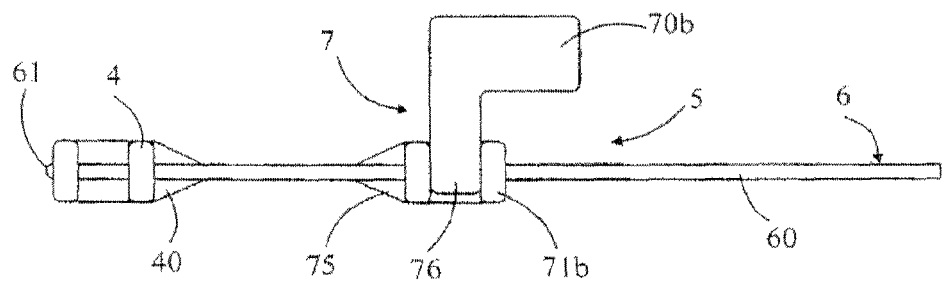
Figure 10:
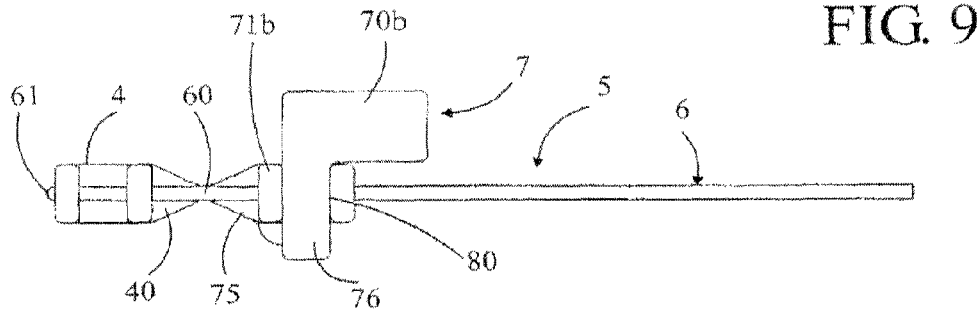

As represented on FIG. 7, hook 76 has the shape of a blade 76a arranged to be inserted in seat 78 and pass through it, said blade 76a showing a shoulder 76b arranged to rest against a lateral side 80 of part 71b. In reference to FIG. 9, when they are assembled, parts 70b and 71b can adopt a position in which the passage openings 77 and 79 are aligned (see FIG. 9), shoulder 76b does not rest on said lateral side 80, and locking element 7 can slide along the free ends 60 of wire 6. Parts 70b and 71b can adopt another position, represented on FIG. 10, in which the passage openings 77 and 79 are offset and shoulder 76b rests on lateral side 80, preventing the removal of hook 76. This position allows locking the free ends 60 of wire 6 in the pressed position that is required.

In the maximum pressed position, the locking element 7 and the positioning element 4 are both resting against the surfaces of the teeth, at the level of a same interproximal gap 9. In this position, the guiding support 3 and the splint 2 are pressed against the surfaces of the teeth 10 and fit their profile.

According to an advantageous feature, parts 70a and 71b have, on their resting area 75, which is supposed to rest against an interproximal gap 9, a triangular cross-section complementary of the natural conformation of this interproximal gap 9, and respectful of the integrity of the gum at the level of this gap 9.

According to another non represented embodiment, the locking element 7 can also consist in a simple sleeve tightly mounted on the free ends 60 of wire 6, this sleeve being for example made out of a material with a high friction coefficient, such as, in particular, a material based on synthetic or natural rubber or similar, and that can also have, in the area intended for resting against the surface of the teeth, a triangular cross-section.

In this variant of the present device 1, it is sufficient to move the sleeve along the ends 60 of wire 6 towards positioning element 4, then to release it when it arrives in contact with teeth 10, at the level of interproximal gap 9. Its position is then maintained simply because of its close contact with wire 6, which is in this case preferably not provided with the above mentioned wax layer.

Figure 5:
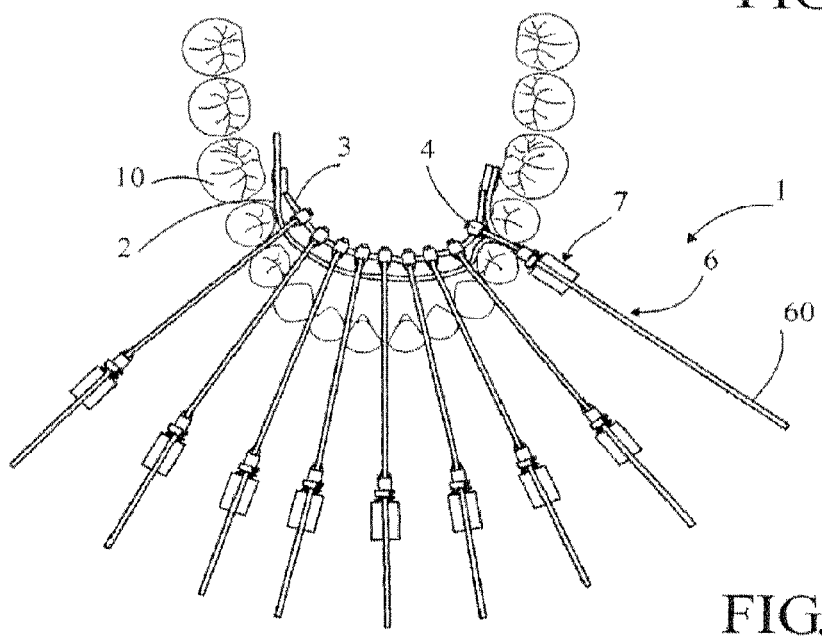

The main steps of the implementation of this device 1 for placing a dental splint 2 are described hereafter, in reference to FIGS. 4 to 6.

FIG. 4 shows how a device 1 carrying a splint 2 is located against dental surfaces, which have been classically subjected previously to phases of cleaning, etching and application of an amelo-dentinal adhesive.

As described previously, splint 2 is assembled on guiding support 3 at the level of two sockets 20, 21, of which at least one (reference 20 on the figures) allows its longitudinal movement with respect to said guiding support 3 thanks to a sliding assembly. It is thus possible to adjust the length of the splint as it is put in place as described below. Splint 2 extends along guiding support 3 passing in the successive loops described by every wire 6.

The different positioning elements 4 are placed each in front of an interproximal gap 9, and the two free ends 60 of the various wires 6 are introduced successively in each of these same interproximal gaps 9. The various locking elements 7 are located on the side of the teeth opposite to said splint 2 and are positioned away from the various positioning elements 4. Device 1 is in a released position (see FIG. 4).

FIG. 5 corresponds to a first step of the implantation process in which, after having applied fluid composite on the surfaces of the teeth, the practitioner begins to bring closer together the locking element 7 and the positioning element 4 located closest to socket 21 in which splint 2 is assembled fixedly on the guiding support 3.

To do so, the practitioner simply moves the locking element 7 along the free ends 60 of wire 6 until the locking element 7 and the positioning element 4 rest on either side against the same interproximal gap 9, as shown on FIG. 5. The practitioner locks this position by screwing part 71a with a female thread on threaded part 70a, or by locking hook 76 of part 70b in seat 78 of part 71b.

Pulling the free ends 60 of wire 6 to bring locking element 7 close to positioning element 4 allows exerting a traction, through wire 6, on the guiding support 3 to bring it closer to the surfaces of the teeth 10, which causes finally the contact between the latter and splint 2. When the locking element 7 is placed in the desired position, it remains there, even after having been released, which allows maintaining the contact between splint 2 and the surface of the teeth 10 without any further intervention of the practitioner, whose hands are then free to carry on with the implantation.

Implantation is then carried out quickly and very simply, since the practitioner now only has to proceed the same way successively to bring progressively the whole of splint 2 in contact with teeth 10, fitting eventually closely their morphology, as shown on FIG. 6. During the placing, the length of splint 2 adapts itself to the profile of the teeth, since at least one of its ends can slide freely in socket 20 of the support.

Finally, after having carried out a classical polymerisation step of splint 2 on the surface of teeth 10, device 1 is removed by opening progressively the various pressing elements 7 of the various positioning elements 4, after having unlocked parts 70a, 71a and 70b, 71b. It is then sufficient to cut off the free ends 60 of wire 6 in an area located between the locking elements 7 and the positioning elements 4, and to remove then splint 2 from the assembly sockets 20, 21.

Figure 11:
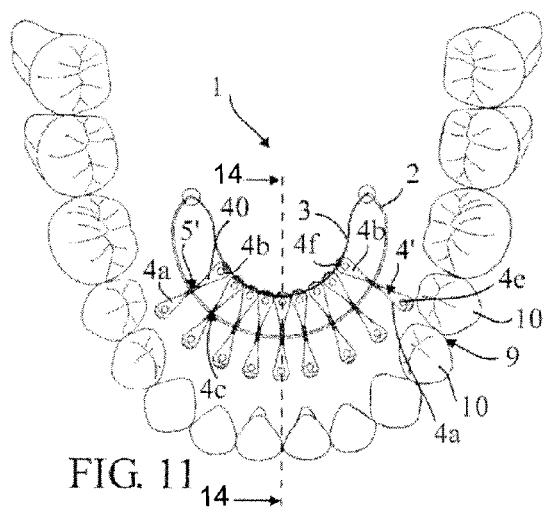
FIGS. 11 to 13 are top views of another embodiment variant of the device according to the invention during its use, at three different stages of the process of placing a dental splint on the internal (lingual or palatal) surfaces of the teeth of a jaw.

FIGS. 11 à 14 illustrate another embodiment variant of a device 1 for placing a dental splint 2 in which the positioning element 4' has a symmetrical structure and comprises two enlarged end sections 4a, 4b connected together by means of a narrow central section 4c.

Figure 14:
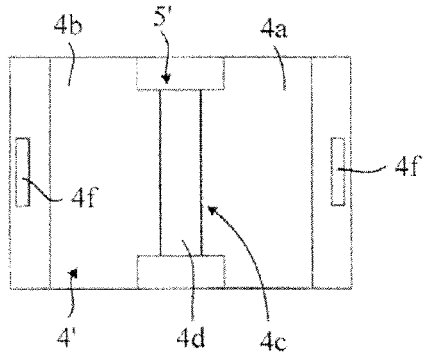
FIG. 14 is a profile view of the positioning element of the device of FIGS. 11 to 13.

As shown on the figures and in particular on FIG. 14, the end section 4b comprises a slot 4f for the passage of the support 3 allowing sliding the positioning element 4' with respect to said support 3. Due to the symmetrical structure of the positioning element 4', the support 3 could also be housed in a slot 4f of end section 4a to allow positioning element 4' to slide. The narrow central section 4c comprises another slot 4d for the passage of splint 2. Consequently, the positioning element 4' is arranged to slide as well with respect to support 3 as with respect to splint 2, which facilitates the adaptation of the latter with respect to the different dental configurations encountered when placing it.

Figure 13:
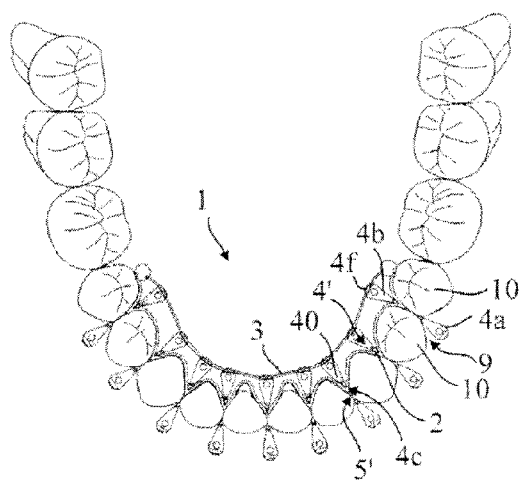

On the other hand, in this embodiment variant, the positioning element 4' is advantageously made of a single part, out of an elastic material such as for example an elastomer, allowing it to adopt a retracted rest position (see FIG. 11) in which end sections 4a, 4b are close to each other and a stretched active position (see FIG. 13) in which end sections 4a, 4b are temporarily distant from each other and central section 4c passes in an interproximal gap 9 in order to bring said splint 2 in contact with the lingual, palatal or vestibular surface of said teeth 10. The central section 4c which stretches as a result of moving away end sections 4a, 4b from each other serves as pressing means 5' for splint 2 on said lingual, palatal or vestibular surfaces of said teeth 10.

As shown on the figures, the end sections 4a, 4b furthermore have, at the level of their front side 40, intended to rest against an interproximal gap, a triangular cross-section allowing a partial introduction of said front side 40 in the interproximal gap 9. Such a structure therefore allows bringing splint 2 against the interproximal gap 9 so that it fits perfectly its shape.

On the other hand; each of end sections 4a, 4b comprises at least one cavity 4e, in this instance only one cavity 4e in the embodiment variant illustrated, arranged to receive an end 101 of a tool such as pliers 100 intended to be used by a practitioner to stretch each positioning element 4' in order to move away from each other end sections 4a, 4b, which makes central section 4c thinner, allowing its introduction in an interproximal gap 9.

Figure 12:
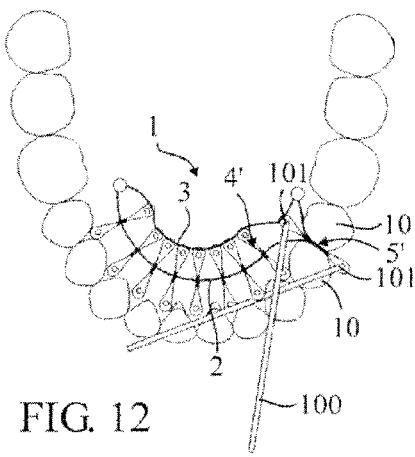

FIG. 11 represents a first step when placing a dental splint 2 on the lingual surfaces of teeth 10, in which the various positioning elements 4' are in their retracted rest position. On FIG. 12, a first positioning element 4', placed in its stretched active position by a practitioner with the help of pliers 100, passes through a first interproximal gap 9. On FIG. 13, the splint 2 fits the lingual, palatal or vestibular surfaces of all concerned teeth 10, the practitioner having proceeded successively to activate progressively all positioning elements 4'.

Finally, after having carried out a classical polymerisation step of splint 2 on the surface of teeth 10, device 1 is removed by cutting each positioning element 4' suitably in the central section 4c.

In a particularly advantageous way from the hygiene point of view, this device 1 is designed based on single-use elements and will thus be thrown away after use. It is of course possible to realise devices that would be reusable after sterilisation. In this case, the choice of materials will be different and suitable for steam sterilisation.

Possibilities for Industrial Application:

This description shows clearly that the invention allows reaching the goals defined, that is to say to allow a practitioner to implant a dental splint in one single session, very easily, saving considerable time, with the possibility to reproduce an optimum result in a systematic way. Such an invention also allows advantageously encouraging a practitioner to opt more frequently for the "direct" placing technique, which is less costly than the "indirect" placing technique and thus more affordable for a larger number of patients.

On the other hand, such a device, suitable for industrial production, can be produced in large quantities, which can also contribute to reducing its cost.

The present invention is not restricted to the examples of embodiment described, but extends to any modification and variant which is obvious to a person skilled in the art while remaining within the scope of the protection defined in the attached claims. In particular, a variant might consist in arranging various positioning elements 4, coupled with pressing elements, directly on a splint 2, which then would serve itself as a guiding support 3.

The invention claimed is:

1. A placing device (1) for placing a dental splint (2), the splint being in the form of one of a flexible wire, tape or grid out of a flexible metallic, a synthetic material or a composite material, the splint (2) being intended to be fixed at the level of the lingual, palatal or vestibular surfaces of at least two adjacent teeth (10) in order to immobilize the at least two adjacent teeth (10) with respect to one another, wherein the placing device (1) comprises at least one flexible and elongated guiding support (3) carrying the splint (2), at least one positioning element (4, 4'), mounted so as to slide on the guiding support (3) behind the splint (2), and arranged for being positioned substantially in front of an interproximal gap (9) between the at least two adjacent teeth (10), pressing means (5, 5') coupled to the positioning element (4, 4') and arranged to bring the positioning element (4, 4') close to the at least two adjacent teeth (10) to be interlocked when pressed in order to bring the splint (2) in contact with the lingual, palatal or vestibular surfaces and fit to their shape and the positioning element (4') comprises two enlarged end sections (4a, 4b) connected together by a narrow central section (4c) which comprises a slot (4d) for the passage of the splint (2), the positioning element (4') is arranged to adopt a retracted rest position in which the end sections (4a, 4b) are close to each other and a stretched active position in which the end sections (4a, 4b) are spaced from one another so that the central section (4c) passes in the interproximal gap (9) in order to bring the splint (2) in contact with the lingual, palatal or vestibular surface of the teeth (10).

2. The device (1) according to claim 1, wherein the positioning element (4') is made of one single part out of an elastic material and in that at least the central section (4c) forms the pressing means (5').

3. The device (1) according to claim 1, wherein the end sections (4a, 4b) have a triangular cross-section, at least at the level of their front side (40), which is intended to rest against the interproximal gap.

4. The device according to claim 1, wherein each of the end sections (4a, 4b) comprises at least one gripping means arranged to allow moving the end sections (4a, 4b) away from one another.

5. The device according to claim 4, wherein the gripping means includes at least one cavity (4e) arranged to receive an end of a tool such as pliers.

6. The device according to claim 1, wherein at least one of the end sections (4a, 4b) comprises a slot (4f) for the passage of the support (3).

7. The device according to claim 1, wherein the guiding support (3) is arranged to define a dental splint.

8. The device according to claim 7, wherein the guiding support (3) is made out of one of a flexible metallic, a synthetic material or a composite material.

9. The device according to claim 1, wherein the device is a single-use device.

* * * * *